United States Patent [19]

Perry et al.

[11] Patent Number: 5,641,962
[45] Date of Patent: Jun. 24, 1997

[54] NON LINEAR MULTIVARIATE INFRARED ANALYSIS METHOD (LAW362)

[75] Inventors: Bruce N. Perry; James M. Brown, both of Flemington, N.J.

[73] Assignee: Exxon Research and Engineering Company, Florham Park, N.J.

[21] Appl. No.: 567,613

[22] Filed: Dec. 5, 1995

[51] Int. Cl.[6] .............................. G01N 21/35; G06F 1/00
[52] U.S. Cl. ........................ 250/339.09; 250/339.09; 250/252.1; 250/339.12; 364/554; 364/573
[58] Field of Search ................ 250/339.09, 252.1 A, 250/339.12; 364/554, 573; 324/76.11

[56] References Cited

U.S. PATENT DOCUMENTS

| | | | |
|---|---|---|---|
| 4,963,745 | 10/1990 | Maggard | 250/339.12 |
| 5,349,188 | 9/1994 | Maggard | 250/339.12 |
| 5,349,189 | 9/1994 | Maggard | 250/339.12 |
| 5,362,965 | 11/1994 | Maggard | 250/339.12 |
| 5,446,681 | 8/1995 | Gethner et al. | 364/554 |

OTHER PUBLICATIONS

Crawford et al., Predicting research octane number from near-infrared absorbance data with neural networks, Elsevier Science Publishers B. V. Amsterdam, pp. 13–20 Apr. 13, 1992.

*Primary Examiner*—Michael J. Tokar
*Assistant Examiner*—Virgil O. Tyler
*Attorney, Agent, or Firm*—Ronald D. Hantman

[57] ABSTRACT

A method for determining a property or composition data of a test sample from a correlation between a calibration sample set and that property or composition data using the spectrum of the test sample, a linear prediction model and a non linear correction to the linear prediction.

9 Claims, 11 Drawing Sheets

NON LINEAR MULTIVARIATE INFRARED ANALYSIS METHOD (LAW362)

BACKGROUND OF THE INVENTION

This invention relates generally to a method for determining physical or chemical properties of materials using infra-red analysis and more specifically to a method for improving the estimation of properties of interest in samples of materials based on non linear correlations to their infra-red spectra.

A particular use of the method is to obtain an improved estimation of octane number of gasolines by infra-red analysis.

Physical or chemical properties such as octane number, cetane number, and aromatics content can be usefully correlated to infrared spectra for appropriate sample sets. Linear techniques such as PLS, PCR, and extensions such as CPSA (Constrained Principal Spectra Analysis, J. M. Brown, U.S. Pat. No. 5,121,337) and the method of DiForggio, U.S. Pat. No. 5,397,899, provide workable correlations in many circumstances. The object of the correlations is to calibrate the infrared analyzer so that it can be employed to estimate the physical or chemical properties of future unknown samples on the basis of their infrared spectra. An important consideration in the implementation of these analyzers is their ability to statistically detect outlier samples, i.e. samples whose analysis represents an extrapolation of the predictive model.

For some applications, linear correlation techniques such as PLS, PCR and CPSA do not provide calibrations that predict physical or chemical properties with sufficient accuracy. Inaccurate calibrations can be an indication that the property being estimated depends in a nonlinear manner on sample composition. Various techniques have been suggested for addressing this problem including localized linear regression, MARS, and Neural Nets, but such techniques generally require large numbers of coefficients to be fit, and generally do not provide the statistical guidance available from linear techniques.

Calibration methods that are currently employed to correlate property or compositional data to spectral data are almost exclusively linear. Such methods assume a linear dependence of the property/component concentration on the spectral signal. Such linear methods are inadequate when the property depends on a nonlinear fashion on chemical components, or when interactions among components cause nonlinear spectral responses. While some nonlinear modeling methods have been explored in the literature, they generally involve attempts to define a nonlinear relationship between the spectral data and the property/component concentration. Such nonlinear methods generally require large numbers of coefficients to be determined. The large number of coefficients requires that very large sample sets be used in the calibration, and is prone to overfitting of the data. Also, most nonlinear methods fail to provide statistical means for determining when a new sample being analyzed is outside the range of the calibration, i.e. outlier detection. A simpler nonlinear method which is less prone to overfitting and which retains outlier detection was needed.

A variety of linear calibrations are in use in estimating property and component concentrations. For example, Hieftje, Honigs and Hirschfeld (U.S. Pat. No. 4,800,279) discussed linear methods for evaluation of physical properties of hydrocarbons. Lambert and Martens (EP 0 285 251) described a linear method for estimating octane numbers. Maggard discussed linear methods for estimating octane numbers (U.S. Pat. No. 4,963,745) and for estimating aromatics in hydrocarbons (U.S. Pat. No. 5,145,785). Brown (U.S. Pat. No. 5,121,337) discusses linear methods based on Constrained Principal Spectra Analysis (CPSA) and gives various examples.

Espinosa, et al. (EP 0 305 090 B1 and EP 0 304 232 A2) describe methods for direct determination of physical properties of hydrocarbons. Espinosa, et al. include linear terms (absorption at selected frequencies), quadratic terms (products between absorptions at different frequencies) and homographic terms (quotients between absorptions at different frequencies) in their equations. While the equations presented in their examples generally contain only a few nonlinear terms, these quadratic and homographic terms were chosen either arbitrarily or statistically from among a large number of possible nonlinear terms. For instance, for the 16 recommended frequencies in EP 0 305 090 B1, there are $18^2$ (324) possible quadratic terms, and another 18×17 (306) possible homographic terms which could have been used. For 16 frequencies, there are 646 coefficients which must be determined or set to zero in deriving the correlations equations. Even for simpler examples where only 6 frequencies were considered, 216 linear, quadratic, and homographic terms are possible, and 216 coefficients must be determined or set to zero in deriving the correlation equations.

Crawford, et al. (Process Control and Quality, 4 (1992) 13–20) predicted research octane number from near-infrared absorbance data with neural networks. Absorbances at 231 wavelengths were used as inputs to a neural network containing 24 nodes in one hidden layer. Including the node biases, a total of 24*231+24 (5568) coefficients (weights and biases) were determined in training the network.

Nonlinear multivariate calibration methods have been reviewed by Sekulic, et al. (Analytical Chemistry, 65 (1993) 835A–845A). Locally weighted regression (LWR), Projection Pursuit Regression (PPR), Alternating Condition Expectations (ACE), Multivariate Adaptive Splines (MARS), Neural Networks, nonlinear Principal Components Regression (NLPCR) and nonlinear Partial Least Squares (NLPLS) are discussed. All these techniques are much more computationally difficult than the nonlinear postprocessing method of the current invention.

SUMMARY OF THE PRESENT INVENTION

The present invention is a method to significantly improve the performance of spectrometer-based analyzers which are used to measure test samples and provide sample property or composition data for process or analytical applications. The method determines property or composition data of a test sample from a nonlinear correlation between the spectrum of the test sample and the value of that property or composition data of the test sample. During the calibration of the analyzer, the method involves the following steps:

(1) the measurement of the spectra of a set of calibration samples, (2) the measurement of property or composition data for said set of calibration samples, (3) the determination of a linear correlation between the spectra from step (1) and the property or composition data from step (2), (4) the determination of linear estimates for the property or composition data for the calibration samples by applying the linear correlation for step (3) to the spectra of the calibration set collected in step (1), and (5) the determination of the nonlinear correction to the linear estimate by fitting the property or composition data from step (2), or the differences between the property or composition data from step (2) and the linear estimates from step (4), as a nonlinear function of the linear estimate from step (4).

During analysis, the nonlinear calibration is used to determine the property or composition data for the tests sample by:

(6) the measurement of the spectrum of the test sample;

(7) the application of the linear correlation determined in step (3) to the spectrum to obtain a linear estimate of the property or composition data;

(8) the application of the nonlinear correction determined in step (5) to the linear estimate in step (7) to estimate the property or composition data of the test sample;

(9) outputting the estimated property or composition data for the test sample determined in step (8).

If the non linear correction in step (5) is calculated by fitting the property or composition data from step (2) directly as a nonlinear function of the linear estimate from step (4), the estimate of the property or composition data for the test sample in step (8) involves substituting the linear estimate from step (7) into the nonlinear correction equation from step (5).

If the nonlinear correction in step (5) is calculated by fitting the differences between the property or composition data from step (2) and the linear estimate of the property or composition data from step (4) as a nonlinear function of the linear estimate from step (4), the estimate of the property or composition data for the test sample in step (8) involves substituting the linear estimate from step (7) into the nonlinear correction equation from step (5), and adding the resultant nonlinear correction to the linear estimate from step (7) to produce the final estimate.

The linear correlation in step (3) involves a linear multivariate calibration developed by regressing the reference property data against variables derived from the spectral data. The spectral variables may be absorbance values at specific wavelengths and the regression method Multilinear Regression (MLR). Alternatively, Principal Components Regression (PCR), Partial Least Squares (PLS), or Constrained Principal Spectra Analysis (CPSA) may be used to extract variables (scores) from the spectral data and to regress these variables against the property data. The residual, i.e. the difference between the actual reference property value and the value predicted by the linear model, is obtained for each sample in the calibration set. The property residuals are then fit as a nonlinear function (e.g. quadratic or cubic function) of the linearly predicted values. Alternatively, the actual reference values can be fit directly as a nonlinear function of the linearly predicted values.

The method can result in significantly improved calibration accuracy and performance of spectrometer-based analyzers, while maintaining the outlier detection capabilities of linear methods.

DESCRIPTION OF THE PREFERRED EMBODIMENT

Figure 1:
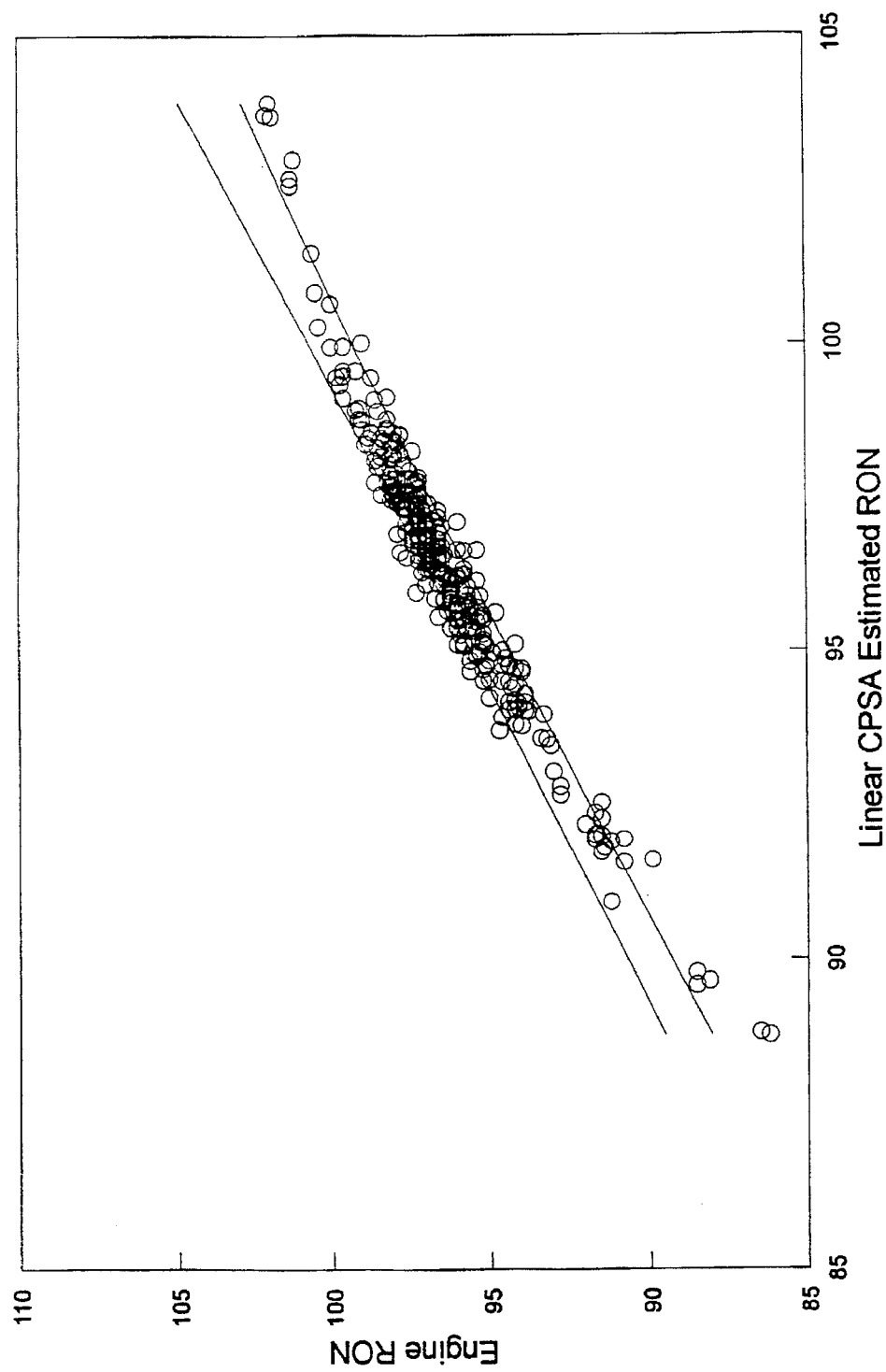
FIG. 1 shows a plot of engine measured Research Octane Number (RON) versus RON estimated via Linear CPSA calibration in Example 1. Circles represent data for 365 Powerformate samples in calibration dataset. Lines are ASTM 95% reproducibility limits for RON Engine measurements calculated relative to linearly estimated RON.

Linear calibration methods have been used to relate spectral measurements to chemical compositions, physical properties, and performance properties. The linear methods are calibrated or trained using a set of samples with known compositions or properties, i.e. samples whose composition or property has been measured by a reference technique. Preferably, the calibration is then validated by applying it for the analysis of a separate test set, and comparing the predicted results to the results produced by the reference method. Finally, the calibrated analyzer is used to analyze unknowns to predict composition or property data.

In the linear calibration, the spectra of the calibration samples form the columns of a matrix X, which is of dimension f by n, where f is the number of individual data points (frequencies or wavelengths) in a spectrum, and n is the number of calibration samples. If the vector y contains the composition/property data for the n calibration samples, then the linear model is built by solving for p in the equation $$y = X^t p \qquad [1]$$

where p is a vector containing the regression coefficients. Since typically, f>>n, equation [1] cannot be solved directly. Three approaches are typically employed. For MLR, k individual rows of X (individual frequencies or wavelengths) are chosen such that k<n, and X is replaced by the smaller matrix $X_k$ containing only the k rows. p is then obtained by calculating the pseudo inverse of the $X_k$ matrix. For PCR, the matrix X is decomposed into the product of three matrices, U (the loadings matrix of dimension f by k), $\Sigma$ (the singular value matrix of dimension k by k), and V (the scores matrix of dimension n by k)

$$X = U \Sigma V^t \qquad [2]$$

The scores are then regressed against the property vector y to form the model. PLS involves a similar decomposition of X into orthogonal matrices and regression of y against a scores matrix.

If x is a vector (dimension f by 1) containing a spectrum, the $\hat{y}_1$ is the estimated property or component concentration for the linear model, and is given by $$\hat{y}_1 = xp \qquad [3]$$

The residuals for the linear model, $r_1$, are given by $$r_1 = \hat{y}_1 - y \qquad [4]$$

If a linear model is adequate to estimate the property y, then the residuals $r_1$ are expected to be normally distributed. If a linear model is inadequate due to a nonlinear dependency between the property being modeled and the sample chemical constituents, then structure will generally be observed in the residuals. In this case, a more accurate model can be obtained by post-processing the estimated value.

The post-processing can take one of two forms. Either the residuals, $r_1$, or the property/composition values, y, are regressed as a nonlinear function of the linearly estimated properties, $\hat{y}_1$.

$$r_1 = f(\hat{y}_1) \qquad [5]$$

or $$y = f(\hat{y}_1) \qquad [6]$$

where $f(\hat{y}_1)$ stands for the nonlinear function of the linearly estimated property/component values. The nonlinear function is preferably a polynomial in powers of the linearly estimated property/component.

$$r_1 = \sum_{i=0}^{m} a_i \hat{y}_1^i \qquad [7]$$

or $$y = \sum_{i=0}^{m} a_i \hat{y}_1^i \qquad [8]$$

If m is 2, then the post-processing is quadratic, and if m is 3, the post-processing is cubic. The choice of m is made based on the ability of the post-processing function to fit the structure observed in the residuals.

If the residuals are fit as a linear function of the linearly estimated properties using [5] or [7], then the nonlinear estimate for the component/property is obtained by summing the linear estimate, and the nonlinearly estimated residual $$\hat{y}_{n1} = \hat{y}_1 + \hat{r} \qquad [9]$$

where $\hat{r}$ the nonlinear estimate for the residual obtained by applying [5] or [7] to the linearly estimated property. If [6] or [8] are used, the nonlinear estimate for the component/property is obtained directly.

The spectral matrix X can be preprocessed prior to the model development by, for instance, mean centering, baseline correction, numerical derivatives, or orthogonalization to baseline and correction spectra (e.g. use of the CPSA algorithm).

A single set of calibration spectra can be used to develop models for multiple properties, each of which can be separately post-processed.

Components that are predicted can include individual chemical species (e.g. benzene), lumped chemical species (e.g. olefins or aromatics), physical properties (e.g. refractive index, specific gravity), chemical properties (e.g. stability) or performance properties (e.g. octane and cetane numbers).

Three examples are given.

EXAMPLE 1

For a dataset of 365 POWERFORMATE samples (reformer product samples), Research Octane Number (RON) was regressed using Constrained Principal Spectra Analysis (CPSA), a linear regression technique. FT-IR spectra were collected at 2 $cm^{-1}$ resolution over the 7000–400 $cm^{-1}$ range on samples contained in a cell having 0.5 millimeter nominal pathelength and calcium floride windows. Absorbances in the frequency ranges from 5300.392–3150.151 $cm^{-1}$, from 2599.573–2445.296 $cm^{-1}$ and from 2274.627–1649.804 $cm^{-1}$ where used in the CPSA calibration. Absorbances in the 7000–5300.392 $cm^{-1}$ range are too weak to contribute signigicantly to the correlation. The frequency ranges from 3150.151–2599.573 $cm^{-1}$ and from 1649.804–400 $cm^{-1}$ are excluded since they contain absorbances that exceed the dynamic response range of the FT-IR instrumentation. The frequency range from 2445.296–2274.627 $cm^{-1}$ is excluded to avoid interferences from atmospheric carbon dioxide. Two sets of polynomial corrections are employed in the CPSA calibration to compensate for baseline variations, one set covering the range from 5300.392–3150.151 $cm^{-1}$, and the second set covering the range from 2599.573–1649.804 $cm^{-1}$. Water vapor corrections are also employed in the CPSA calibration to minimize the effects of variations in instrument purge on the estimated values. Five constrained principal components were used in developing the RON calibration. The coefficients for the five constrained principal components were determined using a PRESS based step-wise regression. A plot of the linearly predicted RON value versus the reference (engine) value is shown in FIG. 1. The standard error of estimate of the data in FIG. 1 is 0.54 RON numbers.

The RON residuals (FT-IR linearly predicted RON minus Engine RON) were regressed against a quadratic function of the linearly-predicted RON. A plot of the RON residuals versus linearly-predicted RON value is shown in FIG. 2, together with a quadratic fit to the residuals.

Figure 2:
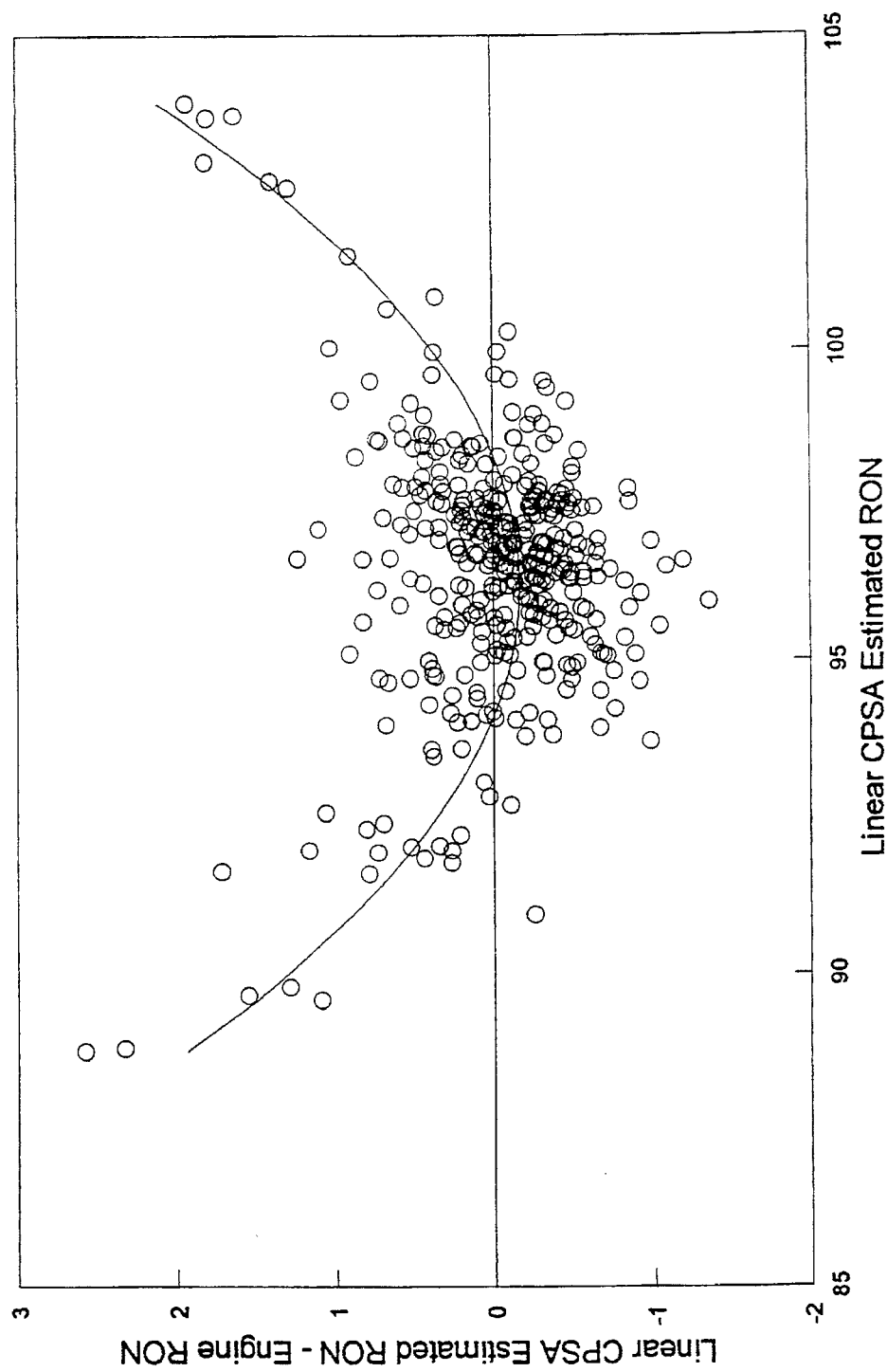
FIG. 2 shows a plot of residuals (RON Estimated via linear CPSA calibration minus RON measured by engine) versus RON estimated via linear CPSA calibration for dataset in Example 1. Circles represent residual values for 365 Powerformate samples in calibration dataset. The line is the cubic polynomial function of the linearly estimated RON which best fits the residuals.
Figure 3:
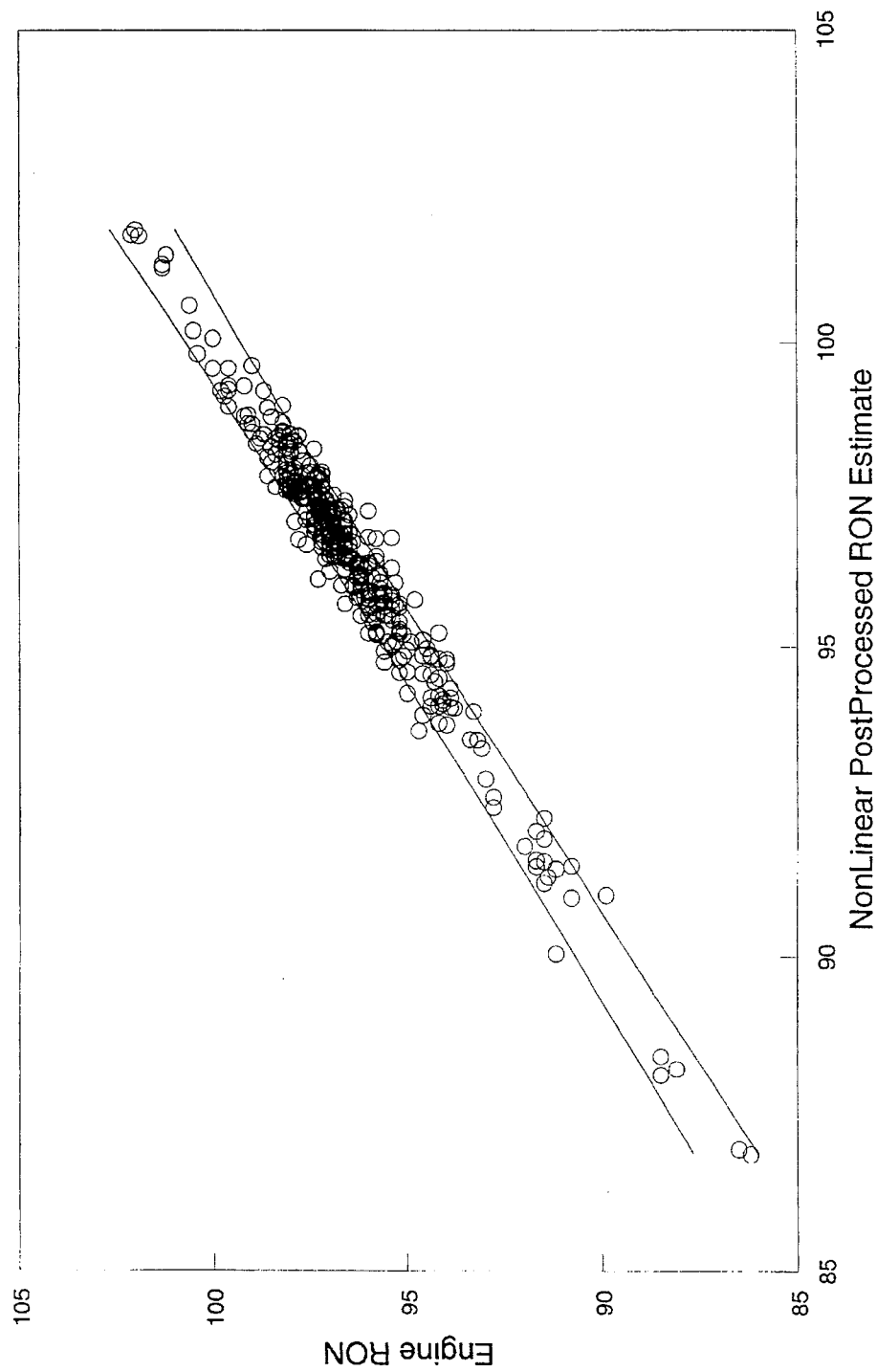
FIG. 3 shows a plot of engine measured Research Octane Number (RON) versus RON estimated via Nonlinear Post-Processing of the Linear CPSA calibration in Example 1. Circles represent data for 365 Powerformate samples in calibration dataset. Lines are ASTM 95% reproducibility limits for RON Engine measurements calculated relative to nonlinearly estimated RON.

FIG. 3 shows the result of the model obtained by applying the quadratic correction of FIG. 2 to the data of FIG. 1. This is equivalent to fitting the reference (engine) RON value as a quadratic function of the linearly predicted RON. The standard error of estimate for FIG. 2 is 0.41 RON numbers.

The nonlinear post-processing method described herein results in a 24% improvement in the RON estimation over the linear method previously used, but requires that only three additional coefficients be determined beyond the five coefficients for the original linear correlation.

EXAMPLE 2

Figure 4:
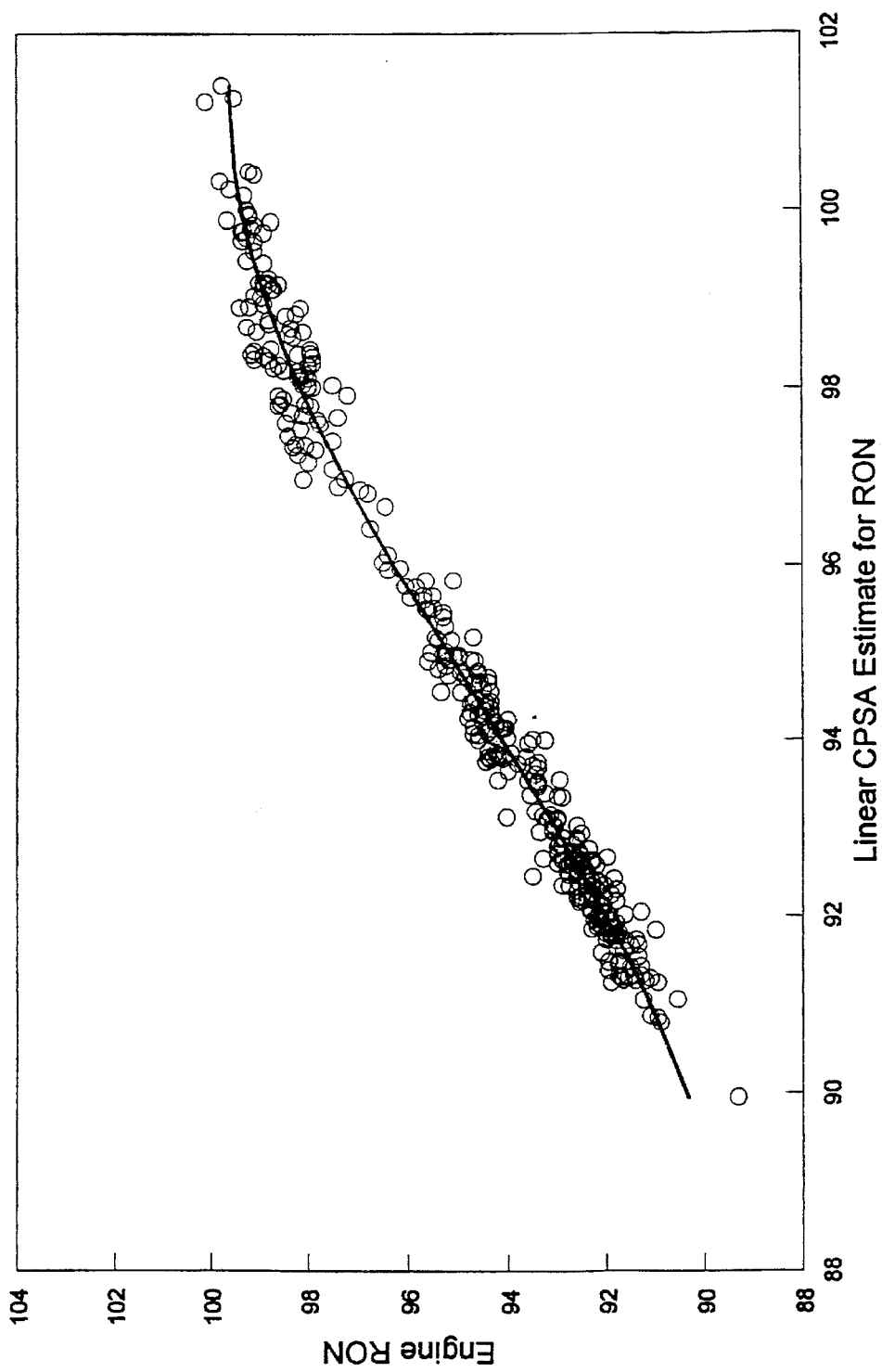
FIG. 4 shows a plot of engine measured Research Octane Number (RON) versus RON estimated via Linear CPSA calibration in Example 2. Circles represent data for 385 blended gasoline samples in calibration dataset. The line represents the cubic polynomial funtion of the linearly estimated RON that is the best fit of the engine RON values.

For a calibration dataset of 385 Blended Gasoline Sample spectra, Research Octane Number (RON) was regressed using Constrained Principal Spectra Analysis (CPSA), a linear regression technique. FT-IR spectra were collected at 2 cm$^{-1}$ resolution over the 7000-400 cm$^{-1}$ range on samples contained in a cell having 0.5 millimeter nominal pathelength and calcium floride windows. Absorbances in the frequency ranges from 4850.094–3324.677 cm$^{-1}$ and from 2200.381–1634.376 cm$^{-1}$ where used in the CPSA calibration. Absorbances in the 7000-4850.094 cm$^{-1}$ range are too weak to contribute signigicantly to the correlation. The frequency ranges from 3150.151–2400 cm$^{-1}$ and from 1634.376–400 cm$^{-1}$ are excluded since they contain absorbances that exceed the dynamic response range of the FT-IR instrumentation. The frequency range from 2400–2200.381 cm$^{-1}$ is excluded to avoid interferences from atmospheric carbon dioxide. Two sets of polynomial corrections are employed in the CPSA calibration to compensate for baseline variations, one cubic set covering the range from 5300.392–3150.151 cm$^{-1}$, and the second quadratic set covering the range from 2599.573–1649.804 cm$^{-1}$. Water vapor corrections are also employed in the CPSA calibration to minimize the effects of variations in instrument purge on the estimated values. Fourteen constrained principal components were used in developing the RON calibration. The coefficients for the fourteen constrained principal components were determined using a PRESS based step-wise regression. A plot of the linearly predicted RON value versus the reference (engine) value is shown in FIG. 4. The Standard Error of Calibration for the linear CPSA model is 0.411.

Figure 5:
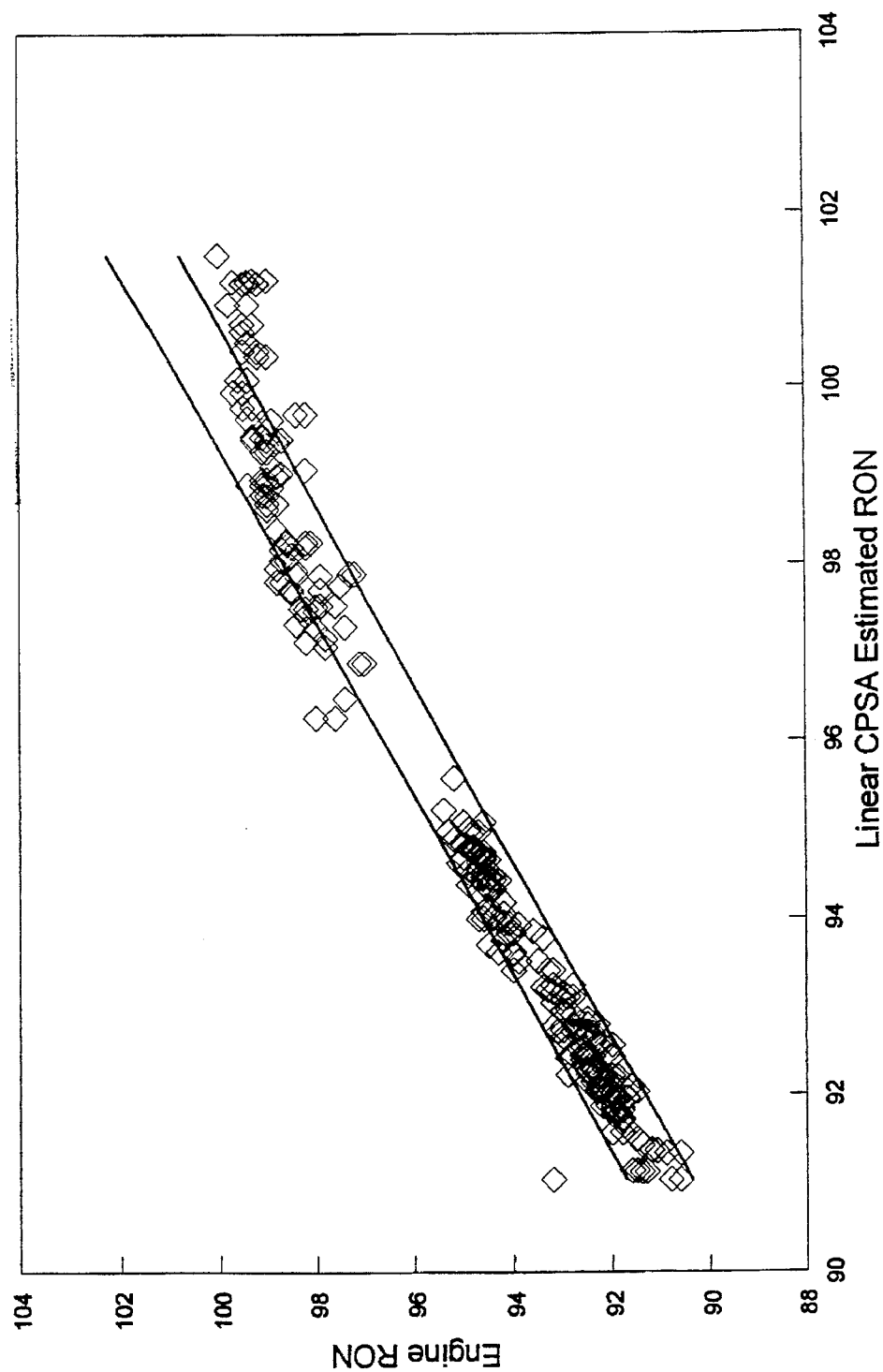
FIG. 5 shows a plot of engine measured Research Octane Number (RON) versus RON estimated via Linear CPSA calibration for test dataset in Example 2. Diamonds represent data for 238 blended gasoline samples in test dataset. Lines are ASTM 95% reproducibility limits for RON Engine measurements calculated relative to linearly estimated RON.

The linear model shown in FIG. 4 was applied for the analysis of 238 Blended Gasoline samples (314 individual engine determinations) which were not in the set of used in the development of the model. The predictions obtained from the linear model for these test samples are shown in FIG. 5. For the linear model, the Standard Error of Validation for the test samples is 0.569, and only 84% of the samples have predicted values that agree with the reference engine values to within the ASTM engine reproducibility limit.

Figure 6:
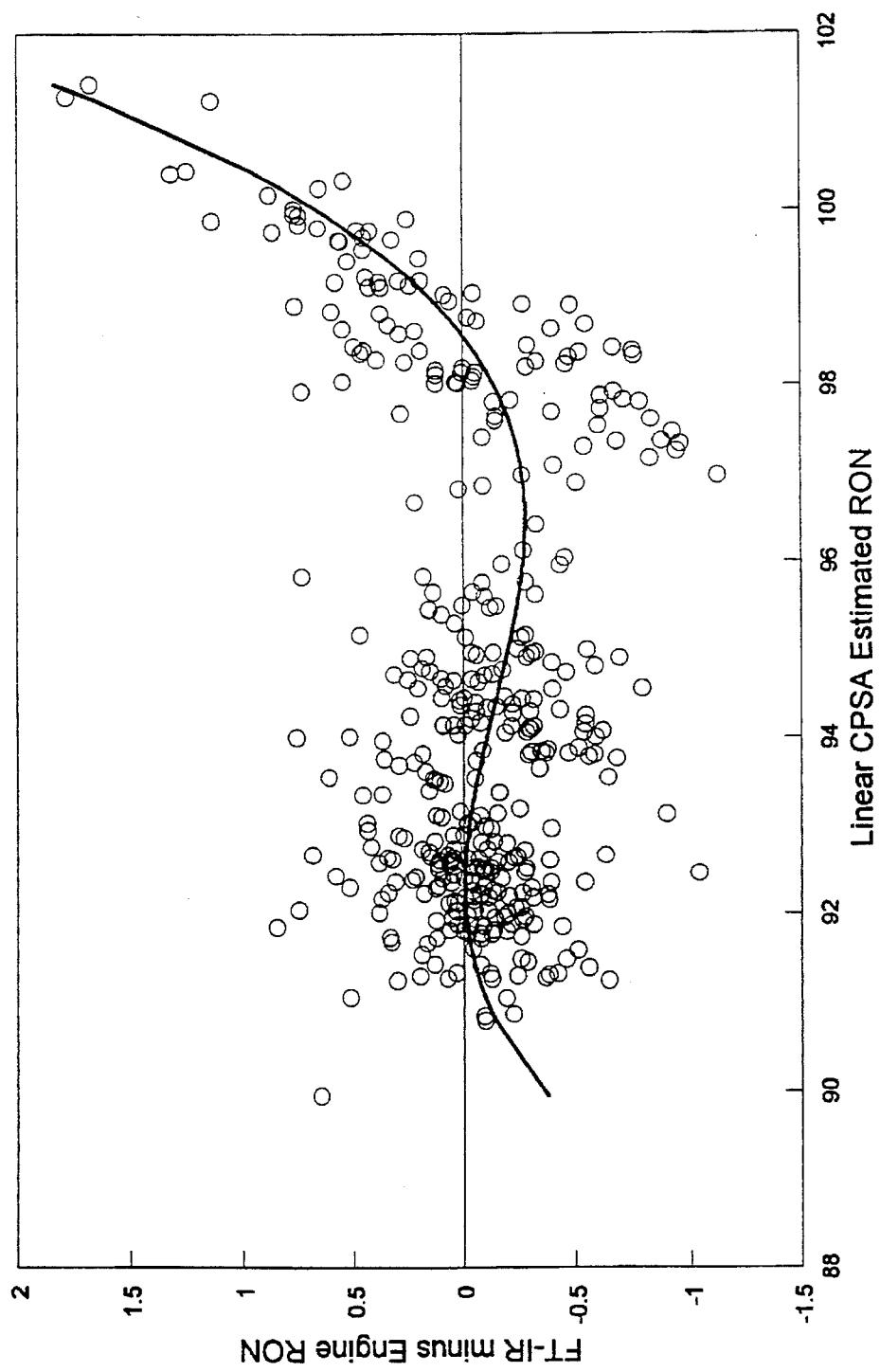
FIG. 6 shows a plot of residuals (RON Estimated via linear CPSA calibration minus RON measured by engine) versus RON estimated via linear CPSA calibration for dataset in Example 2. Circles represent residual values for 385 blended gasoline samples in calibration dataset. The line is the cubic polynomial function of the linearly estimated RON which best fits the residuals.

The RON residuals (FT-IR linearly predicted RON minus Engine RON) for the 385 samples in the calibration set were regressed against a cubic function of the linearly-predicted RON. A plot of the RON residuals versus linearly-predicted RON value is shown in FIG. 6, together with a cubic fit to the residuals. With the cubic post-processing of the linearly estimated RON values, the Standard Error of Calibration is reduced to 0.327.

Figure 7:
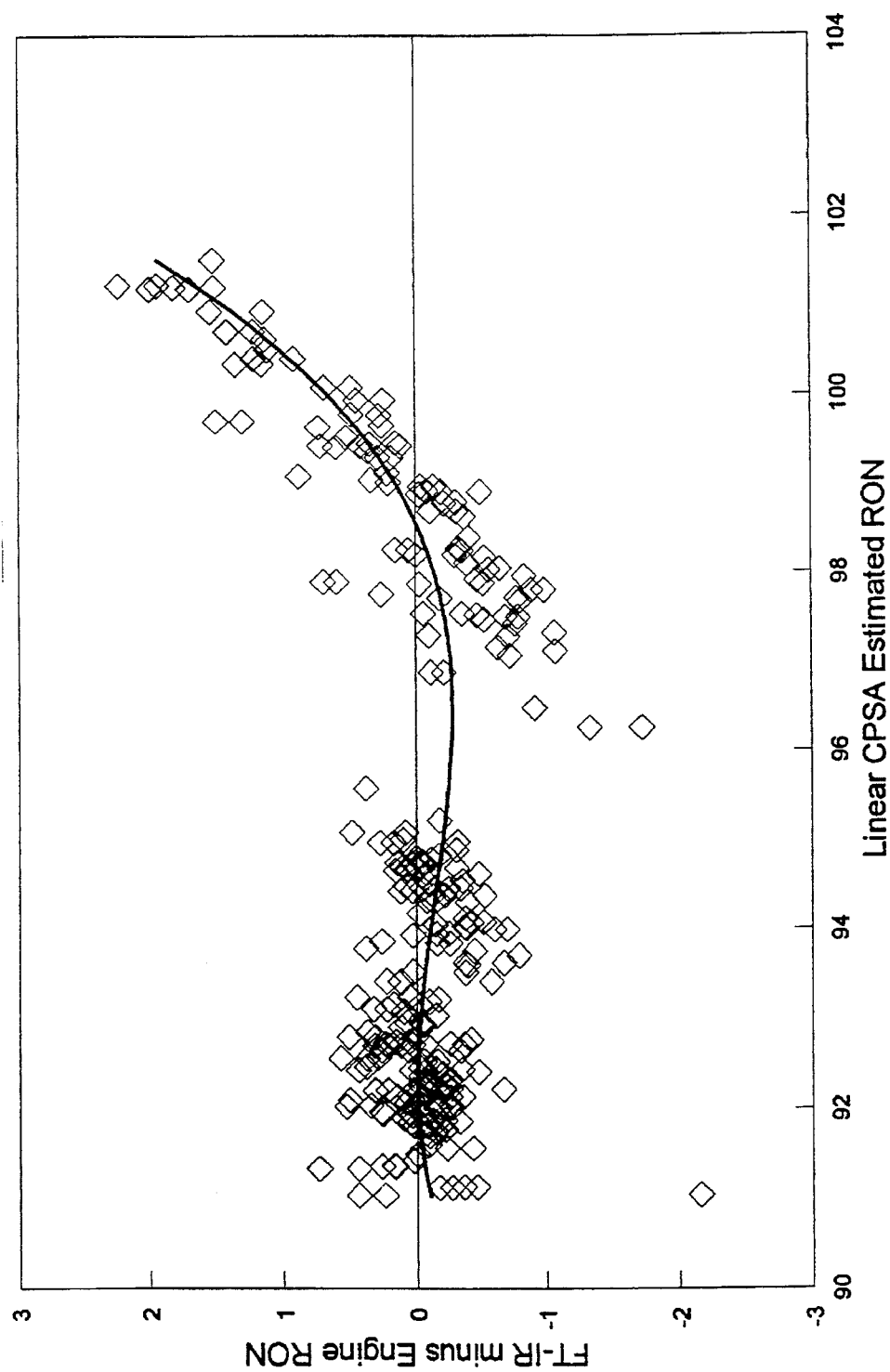
FIG. 7 shows a plot of residuals (RON Estimated via linear CPSA calibration minus RON measured by engine) versus RON estimated via linear CPSA calibration for the test dataset in Example 2. Circles represent residual values for 238 blended gasoline samples in the test dataset. The line is the cubic polynomial function of the linearly estimated RON which was derived from the calibration set.
Figure 8:
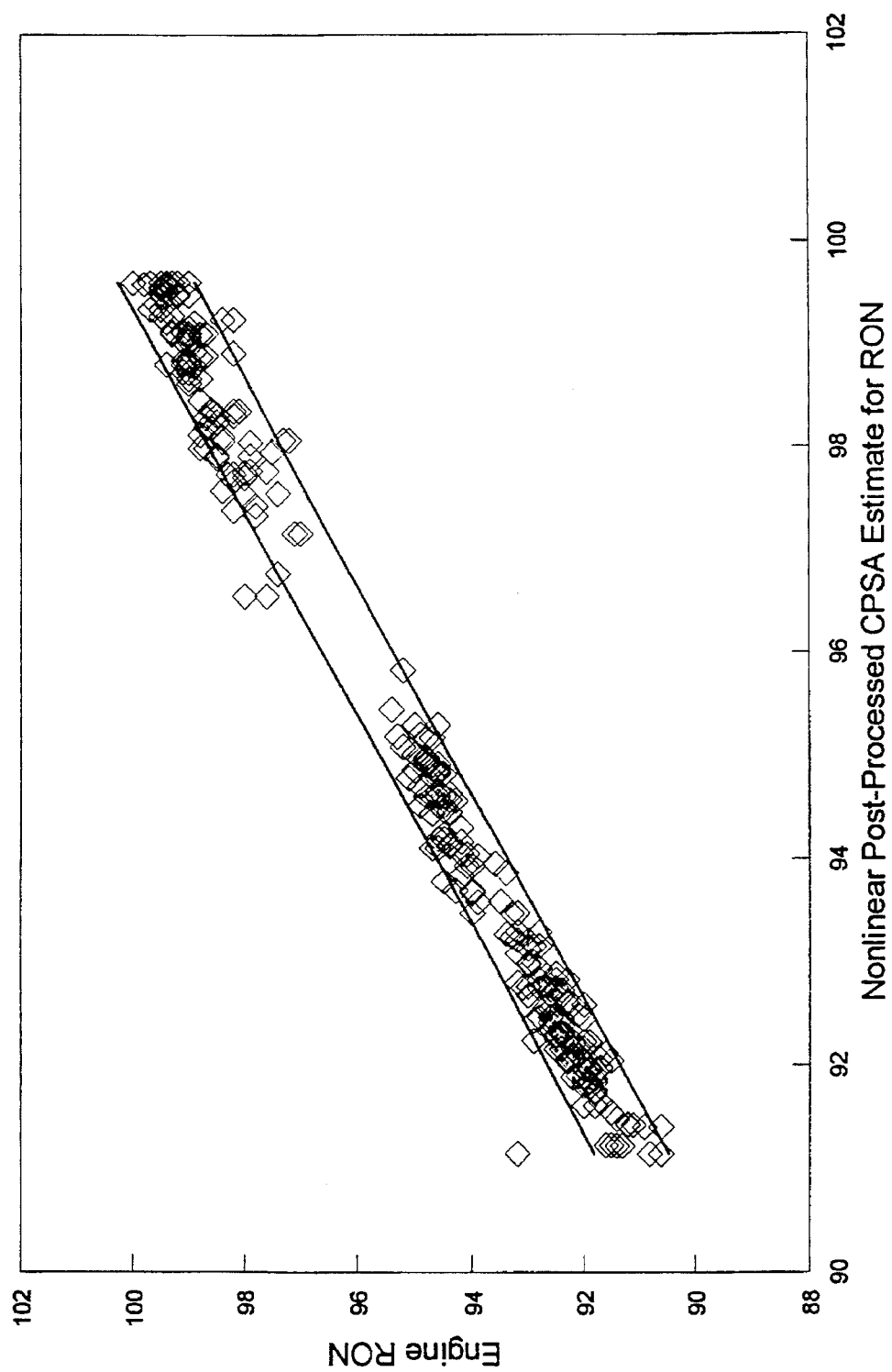
FIG. 8 shows a plot of engine measured Research Octane Number (RON) versus RON estimated via Nonlinear Post-Processing of the Linear CPSA calibration for the test dataset in Example 2. Diamonds represent data for 238 blended gasoline samples in test dataset. Lines are ASTM 95% reproducibility limits for RON Engine measurements calculated relative to Nonlinearly estimated RON.

FIG. 7 shows the RON residuals (FT-IR linearly predicted RON minus Engine RON) for the 238 samples in the test set, plotted against a cubic curve generated using the coefficients derived from the fit of the calibration samples. FIG. 8 shows Engine RON for the test set plotted against the RON values estimated by cubic post-processing of the linearly estimated RON values. With the cubic post-processing, the Standard Error of Validation is reduced to 0.397, and 95% of the estimated RON values agree with the reference engine values to within the ASTM reproducibility of the RON engine.

The nonlinear post-processing method results in a 30% improvement in the RON estimate for the test set, but requires that only 4 additional coefficients be determined beyond those used in the original linear calibration. For ASTM tests such as the D2699 RON test, measurements made by two different operators in two different laboratories are expected to be within the quoted reproducibility 95% of the time. With nonlinear post-processing, the IR RON estimates agree with D2699 RON test data to within the reproducibility 95% of the time demonstrating that the IR estimate is equivalent to the engine determination.

EXAMPLE 3

The same set of 385 Blended Gasoline sample spectra described in Example 2 were used to generate a Multiple Linear Regression (MLR) model according to the method described by Lambert and Martens (EP 0 285 251 B1, Aug. 28, 1991). The absorbances at the frequencies closest to the 15 frequencies given by Lambert and Martens (Table 1) were corrected by subtracting the absorbance at the baseline point, and then were regressed against engine RON values to obtain the coefficients in Table 2. The Standard Error of Estimate for the linear MLR model was 0.459.

TABLE 1

| Frequency in EP 0 285 251 B1 in cm$^{-1}$ | Closest Point in FT-IR Spectra in cm$^{-1}$ |
| --- | --- |
| 4670 | 4670.0238 |
| 4640 | 4639.8915 |
| 4615 | 4615.0625 |
| 4585 | 4584.9302 |
| 4485 | 4484.8910 |
| 4385 | 4385.0928 |
| 4332 | 4332.0600 |
| 4305 | 4305.0615 |
| 4260 | 4259.9835 |
| 4210 | 4210.0845 |
| 4170 | 4170.0688 |
| 4135 | 4135.1153 |
| 4100 | 4099.9208 |
| 4060 | 4059.9051 |
| 4040 | 4039.8972 |
| 4780 (baseline) | 4779.9464 |

Figure 9:
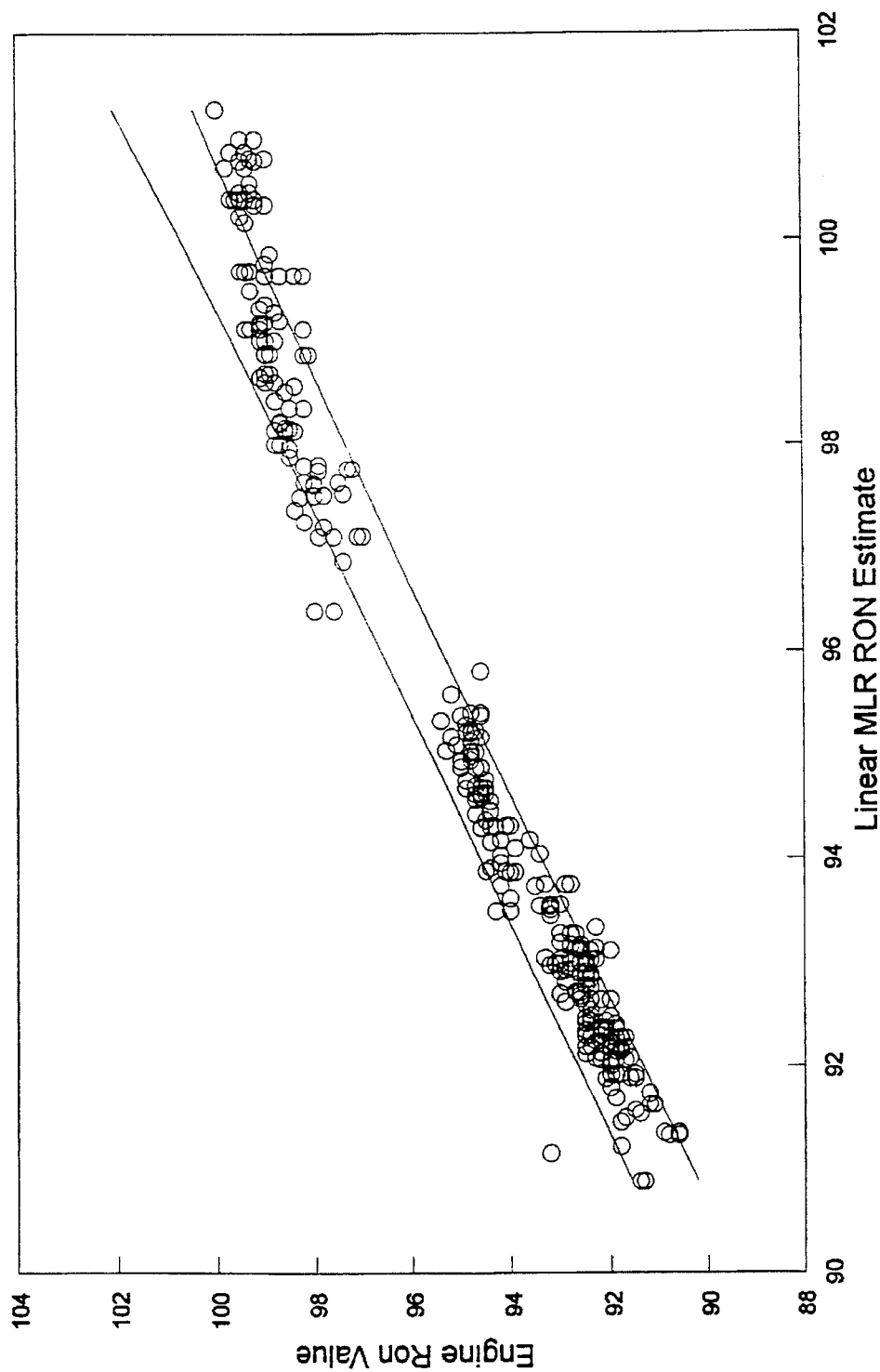
FIG. 9 shows a plot of engine measured Research Octane Number (RON) versus RON estimated via Linear MLR calibration for the test dataset in Example 3. Circles represent data for 238 blended gasoline samples in test dataset. Lines are ASTM 95% reproducibility limits for RON Engine measurements calculated relative to linearly estimated RON.

The MLR model was used to analyze the same set of 238 Blended gasoline test sample spectra. The MLR estimates were compared to the 314 engine determinations for the test set. The predictions from the linear MLR model are shown in FIG. 9. For the linear MLR model, the Standard Error of Validation for the test samples is 0.457, and only 81% of the samples are predicted to within the ASTM engine reproducibility limit.

Figure 10:
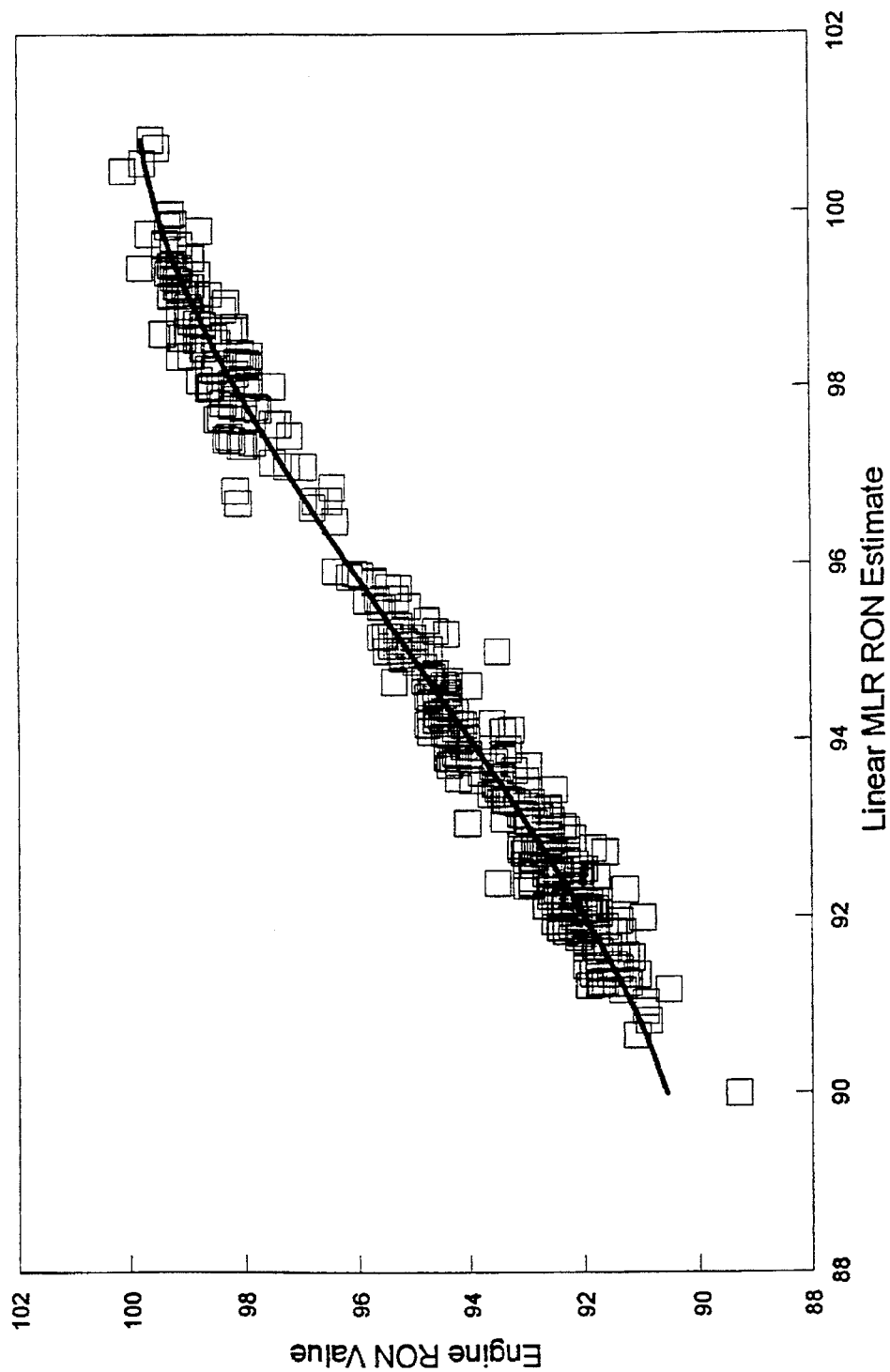
FIG. 10 shows a plot of engine measured Research Octane Number (RON) versus RON estimated via Linear MLR calibration in Example 3. Squares represent data for 385 blended gasoline samples in calibration dataset. The line represents the cubic polynomial function of the linearly estimated RON that is the best fit of the engine RON values.

For the 385 blended gasoline sample calibration set, the engine RON values were fit as a cubic function of the linear MLR estimate. The fit is shown graphically in FIG. 10.

TABLE 2

| Closest Point in FT-IR Spectra in cm⁻¹ | Coefficient in linear MLR Model | Coefficient in EP 0 285 251 B1 |
|---|---|---|
| 4670.0238 | 312.66 | 271.30 |
| 4639.8915 | −188.46 | −0.54 |
| 4615.0625 | −100.30 | −209.08 |
| 4584.9302 | 99.00 | −14.24 |
| 4484.8910 | 90.34 | 16.51 |
| 4385.0928 | 75.70 | 28.84 |
| 4332.0600 | −13.35 | 26.05 |
| 4305.0615 | 31.50 | 16.28 |
| 4259.9835 | −61.07 | 16.03 |
| 4210.0845 | 7.33 | −96.80 |
| 4170.0688 | −95.75 | −25.69 |
| 4135.1153 | 132.72 | 91.10 |
| 4099.9208 | −62.38 | −141.96 |
| 4059.9051 | −20.91 | −27.62 |
| 4039.8972 | −6.70 | 56.30 |
| constant | 93.23 | 94.94 |

Figure 11:
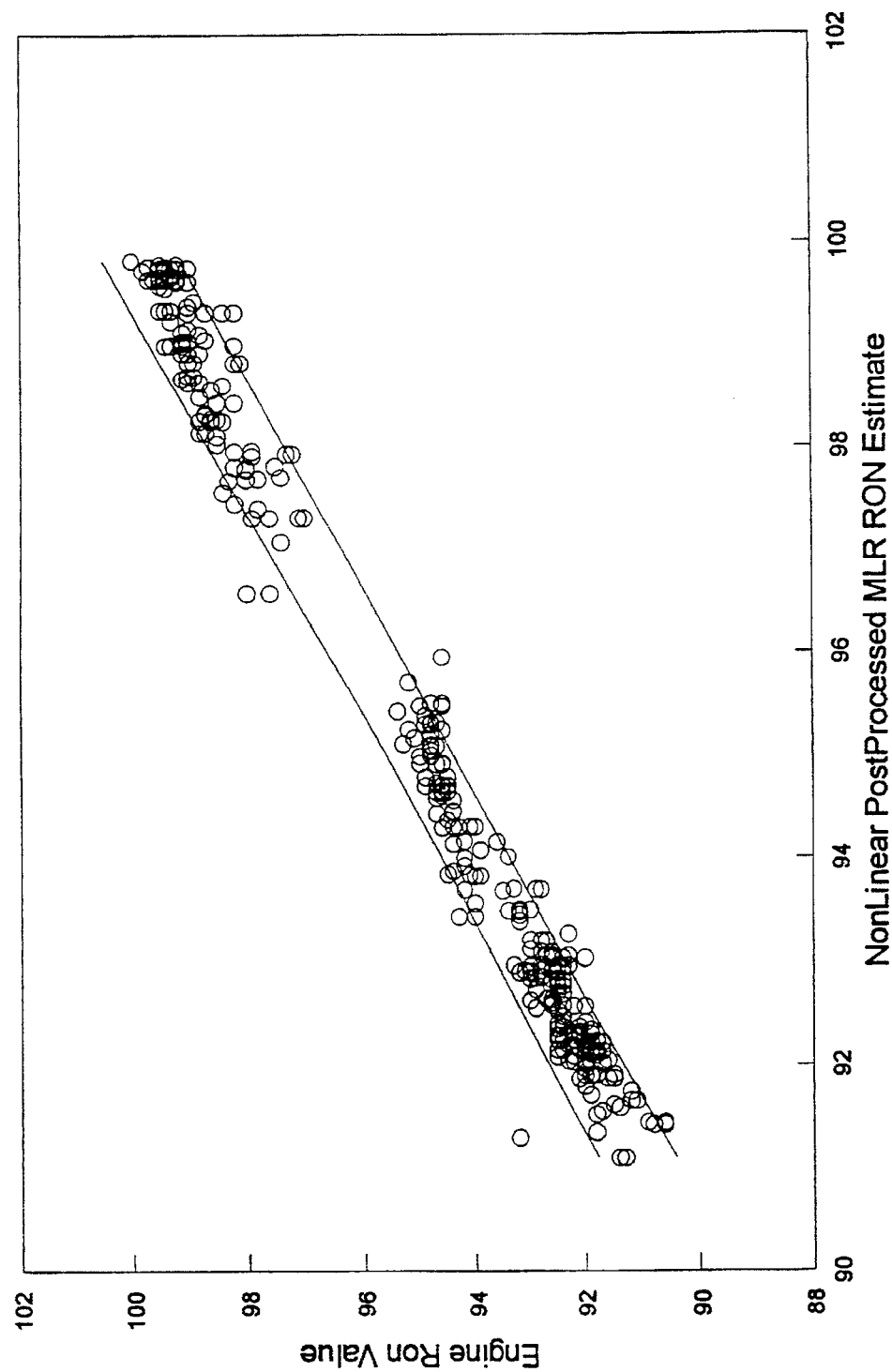
FIG. 11 shows a plot of engine measured Research Octane Number (RON) versus RON estimated via Nonlinear Post-Processing of the Linear MLR calibration for the test dataset in Example 3. Circles represent data for 238 blended gasoline samples in test dataset. Lines are ASTM 95% reproducibility limits for RON Engine measurements calculated relative to nonlinearly estimated RON.

The cubic post-processing was applied to the linear MLR estimates for the test set of 238 blended gasolines. The Nonlinear Post-Processed MLR estimates are compared to the 314 individual engine measurements in FIG. 11. The Standard Error of Validation for the test set is 0.406, and 91% of the samples are estimated to within the reproducibility limits of the ASTM RON test. The cubic Nonlinear Post-processing method results in an improvement of 11% over the linear MLR calibration, but requires only 4 additional coefficients to be determined beyond those used in the linear MLR calibration.

What is claimed is:

1. A method for determining property or composition data of a test sample from a nonlinear correlation between the spectrum of the test sample and the value of that property or composition data of the test sample, comprising analyzing the test sample by
   1. measuring the spectrum of the test sample;
   2. apply a linear correlation to the spectra to obtain a linear estimate of the property or composition data;
   3. applying a nonlinear correction to the linear estimate in step (2) to estimate the property or composition data of the test sample;
   4. outputing the estimated property or composition data for the test sample determined in step (3), wherein the linear correlation and non linear correction are obtained by a) measuring the spectra of a set of calibration samples;

b) measuring property or composition data for said set of calibration samples using a reference method;

c) determining a linear correlation between the spectra from step (a) and the property or composition data from step (b);

d) determining a linear estimate for the property or composition data for the calibration samples by applying the linear correlation of step (c) to the spectra collected in step (b);

e) determining the nonlinear correction to the linear estimate from step (d) by fitting the property or composition data from step (b), or the differences between the property or composition data from step (b) and the linear estimates from step (d), as a nonlinear function of the linear estimate from step (d).

2. A method of claim 1 wherein the nonlinear correction in steps (3) and (e) is calculated by fitting the property or composition data from step (b) directly as a nonlinear function of the linear estimate from step (d), such that the estimate of the property or composition data for the test sample in step (3) involves substituting the linear estimate from step (2) into the nonlinear correction equation from step (e).

3. A method of claim 1 wherein the nonlinear correction in steps (3) and (e) is calculated by fitting the differences between the property or composition data from step (b) and the linear estimate of the property or composition data from step (d) as a nonlinear function of the linear estimate from step (d), such that the estimate of the property or composition data for the test sample in step (3) involves substituting the linear estimate from step (2) into the nonlinear correction equation from step (e), and adding the resultant nonlinear correction to the linear estimate from step (2) to produce the final estimate.

4. The method in claim 1 where the form for the non linear correction is a polynomial.

5. The method in claim 2, where the form for the non linear correction is a polynomial.

6. The method in claim 3, where the form for the non linear correction is a polynomial.

7. The method of claim 1 where the property is research octane number.

8. The method of claim 2 where the property is research octane number.

9. The method of claim 3 where the property is research octane number.

* * * * *